United States Patent [19]
Zugibe

[11] Patent Number: 6,141,977
[45] Date of Patent: *Nov. 7, 2000

[54] APPARATUS AND METHOD FOR RECOVERING VOLATILE REFRIGERANTS

[75] Inventor: Kevin Zugibe, Pomona, N.Y.

[73] Assignee: Hudson Technologies, Inc., Pearl River, N.Y.

[ * ] Notice: This patent is subject to a terminal disclaimer.

[21] Appl. No.: 09/146,590

[22] Filed: Sep. 3, 1998

Related U.S. Application Data

[63] Continuation of application No. 08/766,957, Dec. 16, 1996, Pat. No. 5,802,859.

[51] Int. Cl.[7] ................................................. F25B 45/00
[52] U.S. Cl. ................................ 62/149; 62/125; 62/292
[58] Field of Search ............................. 62/149, 475, 292, 62/125, 293

[56] References Cited

U.S. PATENT DOCUMENTS

| | | | |
|---|---|---|---|
| 5,303,559 | 4/1994 | Severain et al. | 62/77 |
| 5,377,493 | 1/1995 | Friedland | 62/77 |
| 5,493,869 | 2/1996 | Shirley et al. | 62/149 |
| 5,514,595 | 5/1996 | Olds et al. | 436/126 |
| 5,585,023 | 12/1996 | O'Neal | 62/195 |
| 5,647,961 | 7/1997 | Lofland | 203/2 |
| 5,758,506 | 6/1998 | Hancock et al. | 62/77 |
| 5,802,859 | 9/1998 | Zugibe | 62/125 |
| 5,875,638 | 3/1999 | Tinsler | 62/149 |

Primary Examiner—William Doerrler
Assistant Examiner—Melvin Jones
Attorney, Agent, or Firm—Milde, Hoffberg & Macklin, LLP

[57] ABSTRACT

A self-contained refrigerant recovery device for recovering refrigerant from a transfer vessel into a storage reservoir, comprising, in a single enclosure a qualitative analyzer for determining a quality of a refrigerant in the transfer vessel; a quantitative analyzer for determining a quantity of refrigerant in the transfer vessel; a refrigerant extractor for withdrawing refrigerant from the transfer vessel into a storage reservoir; an accounting system for determining a value of refrigerant in the transfer vessel based on the qualitative analysis and the quantitative analysis; and an output for outputting said value. The system preferably has a plurality of storage reservoirs, the refrigerant being withdrawn from the transfer vessel into one of said plurality of storage reservoirs based on said qualitative analysis. In operation, a single connection between the transfer vessel and the recovery device is sufficient.

20 Claims, 5 Drawing Sheets

APPARATUS AND METHOD FOR RECOVERING VOLATILE REFRIGERANTS

The present application is a continuation of U.S. patent application Ser. No. 08/766,957, filed Dec. 16, 1996, issued as U.S. Pat. No. 5,802,859 on Sep. 9, 1998.

FIELD OF THE INVENTION

The present invention relates to the field of refrigerant recovery apparatus and methods, and more particularly to a point of sale device for qualitatively and quantitatively analyzing refrigerant compositions and withdrawing such refrigerant from a closed transfer vessel into a mass storage reservoir.

BACKGROUND OF THE INVENTION

A wide variety of mechanical refrigeration systems are in use currently in a wide variety of applications. These applications include refrigerators, heat pumps, and air conditioners used both in vehicles and in buildings. The vast majority of mechanical refrigeration systems operate according to similar, well known principles, employing a closed-loop fluid circuit through which refrigerant flows.

Refrigerants are liquid substances that vaporize at low temperatures and are used in mechanical systems to deliver a cooling effect or for heat transfer. Refrigerants absorb heat via evaporation from one area and reject it via condensation into another area. A desirable refrigerant provides an evaporator pressure as high as possible and, simultaneously, a condenser pressure as low as possible. High evaporator pressures imply high vapor densities, and thus a greater system capacity for a given compressor. However, the efficiency at the higher pressures is lower, especially as the condenser pressure approaches the critical pressure. It has generally been found that the maximum efficiency of a theoretical vapor compression cycle is achieved by fluids with low vapor heat capacity, associated with fluids with simple molecular structure and low molecular weight.

Refrigerants must satisfy a number of other requirements as best as possible including compatibility with compressor lubricants and the materials of construction of refrigerating equipment, toxicity, environmental effects, cost availability, and safety.

The fluid refrigerants commonly used today typically include halogenated and partially halogenated alkanes, including chlorofluorocarbons (CFCs), hydrochlorofluorocarbons (HFCFs), and less commonly hydrofluorocarbons (HFCs) and perfluorocarbons (PFCs). A number of other refrigerants are known, including propane and fluorocarbon ethers. Some common refrigerants are identified as R11, R12, R22, R500, and R502, each refrigerant having characteristics which make it suitable for different types of applications. Because of the different temperature requirement sin different industries, differing refrigerants having different boiling points may all be brought to the same distributor. For example, R22 is of particular interest in that it is commonly used in commercial air conditioning systems, which often must be purged to conduct repairs. This R22 is collected in transfer vessels, also known as recovery cylinders, which hold about 30–50 pounds of refrigerant. This refrigerant is generally mixed with compressor lubricant oil, and may be contaminated with water, grit, or other materials.

During usage, it is important that the refrigerants be kept relatively free of contaminants, including foreign matter such as particulates, water and air. It is vital that hermetic integrity of the refrigerant system be maintained, both to retain the refrigerants and to prevent influx of undesired elements. When the refrigerants become contaminated, though influx of undesired elements, or breakdown of components, it becomes necessary to replace or purify the refrigerants. Contaminants within a refrigerant are thus substances that render the refrigerant impure. They include gaseous substances such as non-condensables, liquids such as water and solid particulates such as metal fillings. Contaminants also include chloride ions, acids and various other residues that result when hermetically sealed compressor motors fail while electrically charged, often with burned wire insulation. Contamination is generally measured via various laboratory instruments. Air conditioning/refrigeration original equipment manufacturers and standards organizations specify the percent of contamination allowable within equipment.

Mechanical refrigeration systems periodically require servicing. This servicing often takes the form of the addition of refrigerant into the system to replace refrigerant which has escaped from the system. Other servicing often takes the form of repairs to, or replacements of components in the system such as compressors, evaporators, filters, dryers, expansion valves and condensers.

Before adding refrigerant, or repairing or replacing one or more components, it is often necessary to remove the refrigerant remaining in the system. Typically, this remaining refrigerant is removed and stored in transfer vessels.

Transfer vessels are U.S. Department of Transportation ("U.S. D.O.T.") approved metal container used for the withdrawal, storage and transport of recovered refrigerants. They are certified by the manufacturer to withstand the design ratings required by the U.S. D.O.T. Transfer vessels are also known as recovery vessels, recovery cylinders, returnable shipping containers or simply "cylinders". Recovery cylinders are manually carried to the recovery site hence are typically restricted to the 30–50 lb. weight capacity classifications. These are specific labeling regulations for recovery cylinders and they are painted gray with yellow tops. These cylinders are generally characterized by a combined liquid/vapor valve located on top and many are equipped with reed switches that are used to shut off recovery equipment upon reaching maximum fill, which is a liquid level of 80%. A dip tube is employed internally to allow liquid removal without inverting the cylinder. However, this dip tube often does not allow complete withdrawal of liquid refrigerant from the transfer vessel. Typically, transfer vessels are not feature-rich, as they may be subject to exchange or substantial hiatus during processing. Therefore, sophisticated couplings, valves, gauges and the like are not commonly included, and the dip tubes, discussed below, may be inoperative or only partially functional. Because of the exchange or delay, these transfer vessels generally meet a "least common denominator". According to the present invention, the transfer vessel is immediately returned to the user, so that advanced features, such as quick connect couplings, gauges, highly functional dip tubes, high quality valves and the like may be included. For example, a quick-connect valve will save time and wear on the valve fitting, a distant concern for an exchange transfer vessel.

Dip tubes 3 are employed by the refrigerant recovery industry to provide an expeditious evacuation of a transfer vessel 1. The dip tube 3 is generally a metal or plastic hollow elongated cylindrical structure located internal to the transfer vessel 1. An external valve assembly 4 is mounted on top of the tank, from which the dip tube 3 extends downward.

The dip tube's other end is as close to the transfer tank's bottom as feasible without risking blockage by the bottom or perhaps solid contaminants. Operation of the externally mounted valve 4 allows liquid refrigerant to be sucked or drawn out of the transfer vessel 1 without manually inverting the cylinder. A full transfer vessel 1 holds 80% of its volume in the liquid phase 2 with the remaining 20% at the top in a gaseous state. Without a dip tube 3, a top-only withdrawal process would be time consuming due to the differing densities and the need to vaporize refrigerant for withdrawal from the transfer vessel and then recondense it.

Hose fittings used for refrigerant recovery have been standardized to assist the development of the industry, and to prevent accidental filling of a transfer vessel with the wrong contents. The standard transfer vessel will mate with a SAE standard J639 fitting, which is 7/16 inch, 20 thread and is used for all common refrigerants except R-134a. The fitting on the transfer vessel is generally formed of brass.

Typically, a transfer vessel 1 filled with recovered refrigerant 2 is brought to a distributor. The distributor holds the transfer vessel for a recycler, who transports the transfer vessel to its facility. At the facility, as shown in FIG. 1, the content of the transfer vessel 1 is first connected to a fitting 7 and qualitatively analyzed for content by a qualitative analyzer 10 to determine a type and purity of the refrigerant 2. The transfer vessel is then disconnected from the qualitative analyzer 10, and the weight of the transfer vessel 1 is then recorded from a scale 19. The transfer vessel 1 is then connected to another fitting 8, and the refrigerant 2 removed, using an evacuation pump 12 and transferred into a storage reservoir 15. After complete evacuation, the weight of the transfer vessel 1 is again measured using the scale 19, and the difference calculated. The value of the refrigerant 2 is then calculated based on the qualitative analysis, weight, and attributed value. In this system, the valve 4 must be connected to two different fittings 7, 8, and the value calculated from various device outputs.

Infrequently, refrigerants may become mixed or mislabeled. Such mixtures may be very difficult to separate or reclaim, and further a small amount of an inappropriate or contaminating refrigerant may contaminate a large amount of pure refrigerant. This contamination makes the entire lot unsuitable for use and requires expensive purification of the entire lot. The costs involved in remediating such potential contamination are such that the transfer vessels are normally transported to a recycling facility for testing before they are admixed into larger containers. This leads to the problems that each separate transfer vessel must be shipped from a distributor's office or facility, tracked and the value accounted for, and then the emptied transfer vessels must be reshipped back to their owner or originator.

It is believed that refrigerants, especially chlorofluorocarbons (CFCs), used in vapor compression cooling systems (i.e., refrigeration systems) have a detrimental effect on the ozone layer of the earth's atmosphere when released from the refrigeration system into the environment. To this end, Federal legislation has been exacted, commonly referred to as the Clean Air Act, that has mandated strict requirements directed toward eliminating the release of CFCs into the atmosphere. In fact, after Jul. 1, 1992 Federal Law make it unlawful for any person in the course of maintaining, servicing, repairing and disposing of air conditioning or refrigeration equipment, to knowingly vent or otherwise release or dispose of ozone depleting substances used as refrigerants, and imposes stiff fines and penalties will be levied against violators.

The refrigerant management business is thus subject to extensive, stringent and frequently changing federal, state and local laws and substantial regulation under these laws by governmental agencies, including the EPA, the United States Occupational Safety and Health Administration and the United States Department of Transportation. Among other things, these regulatory authorities impose requirements which regulate the handling, packaging, labeling, transportation and disposal of hazardous and nonhazardous materials and the health and safety of workers.

Pursuant to the Clean Air Act, a recovered refrigerant must satisfy the same purity standards as newly manufactured refrigerants in accordance with standards established by the Air Conditioning and Refrigeration Institute ("ARI") prior to resale to a person other than the owner of the equipment from which it was recovered. The ARI and the EPA administer certification programs pursuant to which applicants are certified to reclaim refrigerants in compliance with ARI standards. Under such programs, the ARI issues a certification for each refrigerant and conducts periodic inspections and quality testing of reclaimed refrigerants. The ARI standards define a level of quality for new and reclaimed refrigerants which can be used in new or existing refrigeration and air-conditioning equipment. The standard is intended to provide guidance to the industry, including manufacturers, refrigerant reclaimers, and the like. Contaminated refrigerant can result in the failure of refrigeration system components such a the compressor.

To avoid releasing these fluorocarbons into the atmosphere, devices have been constructed that are designed to recover the refrigerant from the refrigeration system. Examples of such a refrigerant recovery devices are shown in U.S. Pat. Nos. 4,942,741; 4,285,206; 4,539,817; 4,364,236; 4,441,330; 4,476,668; 4,768,347; and 4,261,178.

The increasing cost of CFC refrigerants and the prohibition against environmental release have created a need for effective refrigerant recycling, recovery and reclamation equipment (hereinafter referred to as "recycling equipment"). In general terms, recycling equipment collects and reuses the refrigerant of a refrigeration system that has broken down and is need of repair or one that simply requires routine maintenance involving the removal of refrigerant. However, it should be noted that the terms "recover," "recycle" and "reclaim" have significantly distinct definitions in the art and that each definition connotes specific performance characteristics of a particular piece of recycling equipment.

"Recover" means removing refrigerant, in any condition, from a system and storing it in an external container without necessarily testing or processing it in any way. Recovery processes are well known, and often the refrigerant is recovered during system repair and used to recharge the source system after repair. Thus, where for some reason the source system is not immediately recharged, the recovered refrigerant, which is often not particularly contaminated, is removed. "Recycle" means to clean recovered refrigerant for reuse by separating moisture and oil and making a single or multiple passes through devices, such as replaceable core filter-dryers, which reduce moisture, acidity and particulate matter that have contaminated the refrigerant. A recycling system does not seek to separate mixed refrigerants or to assure product purity. Finally, "reclaim" means to reprocess the recovered and/or recycled refrigerants to new product specifications by means which may include distillation. Chemical analysis of the refrigerant is typically required to determine that appropriate product specifications are met. Thus, the term "reclaim" usually implies the use of processes or procedures available only at a reprocessing or manufacturing facility. However, portable reclamation systems are available.

There are a number of known methods and apparatus for separating refrigerants, including U.S. Pat. Nos. 2,951,349; 4,939,905; 5,089,033; 5,110,364; 5,199,962; 5,200,431; 5,205,843; 5,269,155; 5,347,822; 5,374,300; 5,425,242; 5,444,171; 5,446,216; 5,456,841; 5,470,442; and 5,534,151. In addition, there are a number of known refrigerant recovery systems, including U.S. Pat. Nos. 5,222,369; 5,226,300; 5,243,831; 5,245,840; 5,263,331; 5,272,882; 5,277,032; 5,313,808; 5,327,735; 5,353,603; 5,359,859; 5,363,662; 5,379,607; 5,390,503; 5,442,930; 5,195,333; 5,189,889; 5,176,008; 5,167,126; 5,032,148; and 5,044,166. Also known are refrigerant property analyzing systems, as shown in U.S. Pat. Nos. 5,371,019; 5,469,714; and 5,514,595.

After a period of use, refrigerants are commonly contaminated with compressor oil, water, other refrigerants, and various contaminants. In this case, contractors and HVAC maintenance workers must transfer used refrigerant into a transfer vessel, which, if not returned to the source refrigeration system, is then returned to a distributor. Generally, the distributor presently provides a receipt for the vessel, which is then shipped to a recycler/reclaimer, who qualitatively assays the refrigerant and determines the quantity. The qualitative assay and amount determine the value of the used refrigerant, which is then accounted to the source of the refrigerant. This known process is cumbersome, requiring the distributor, contractor or HVAC maintenance company to have multiple refrigerant transfer vessels available during the shipping analysis and return of the emptied vessel. Further, there may be a substantial accounting delay.

U.S. Pat. No. 5,231,841 relates to a refrigerant charging system which determines the mass amount of refrigerant charged by determining the volume of refrigerant charged, the density of the refrigerant based on its pressure as it is charged, and determines the mass amount charged from the determined density and pressure. The apparatus has a pressure compensated flow valve and determines the volume of refrigerant charged based on the amount of time refrigerant has flowed through the constant flow valve. The type of refrigerant being charged can be selected from a plurality of refrigerant types and the apparatus has a memory in which data related to density and flow characteristics of each refrigerant type is stored. The apparatus uses the data for the selected refrigerant to determine the mass amount of refrigerant charged. The apparatus further determines that the refrigerant supply tank is empty when its pressure decay exceeds a predetermined amount. The apparatus has a manifold in which the constant flow valve is mounted and the apparatus can be made as a portable, hand carried unit. The apparatus can also be used as a mass flowmeter.

Thus, there is a need for an apparatus and method for immediately valuing and removing refrigerant from a transfer vessel at a point of sale location, without need for many manual steps by the operator.

SUMMARY OF THE INVENTION

The present invention therefore provides a system which qualitatively and quantitatively analyzes refrigerant in a transfer vessel to determine a value, evacuates the transfer vessel and accounts for the value.

This allows on-site verification of the lack of contamination of the contents of a transfer vessel, and complete emptying of the transfer vessel at a distributor's facility, with immediate accounting and return of the transfer vessel to the originator. Thus, time, shipping expense, tracking efforts and accounting efforts are all minimized.

In general, the basic respective subfunctions of the present system and method are known. Thus, the qualitative analysis is similar to that performed by recyclers/reclaimers presently, and may include typical types of analyzers presently employed. The quantitative analysis is generally weight based, and thus is also known in the art. Typically the starting and ending weight of a transfer vessel is determined by an electronic scale, with the difference indicating the amount of refrigerant removed. Further, transfer vessel evacuation systems and technology are well known. Typically, the dense fluid phase is removed first by use of a dip tube or by inverting the transfer vessel so that the valve is at the bottom. After the dense fluid phase is removed, the vapor phase is drawn to a relatively high vacuum and removed from the vessel.

The present invention therefore provides the integration of these functions into a single system which eliminates the need for separate manual operations of analysis, evacuation and accounting, and allows operation through a single valve manifold.

The present invention therefore provides a system which is self contained and automated, for use in a point of sale environment by refrigeration workers. In this case, a worker presents a transfer vessel containing refrigerant at a point of sale, e.g., at a distributor's facility. The system initially withdraws a small sample of the refrigerant for qualitative analysis, which may be performed by infrared, chromatographic, or other known means. The quantitative analysis determines the type of refrigerant and its purity, as well as the presence of any significant or unexpected contaminants. Based on this qualitative analysis, a value may be determined. The quantity of refrigerant is then determined. This may be by weighing the vessel before and after evacuation, or by determination of a quantity of refrigerant inside the apparatus during or subsequent to evacuation. Based on the quantitative and qualitative analysis, a value of the refrigerant is determined and accounted for. For example, a paper receipt, electronic monetary transfer, account credit, or visible display at a cash register may be generated. Further, the value may be encoded on a "smart card" or magnetic stripe on a credit-type card. The contents of the transfer vessel are completely evacuated, and the vessel is available for reuse.

The transfer vessel is fitted with a valve assembly which includes a dip tube. The valve assembly on the transfer vessel is often fabricated from brass, which is easily worked and relatively resistant to corrosion. The standard transfer vessel will mate with a SAE standard J639 fitting, which is 7/16 inch, 20 thread, which is used for all common refrigerants except R-134a. According to a preferred embodiment, the mating fitting is formed of stainless steel, which is more durable than brass and therefore less likely to fail or become damaged. The transfer vessel may be connected to the system of the present invention through a valve which accesses the space within the transfer vessel through the dip tube, or alternatively the transfer vessel may be inverted and the connection made through the dip tube, or alternatively the transfer vessel may be inverted and the connection made through what is normally a "vapor port", but which in the inverted position releases the dense fluid refrigerant first.

Ideally, the valve manifold for initially sampling the refrigerant quality and subsequently allowing refrigerant withdrawal, and which interconnects to the mating fitting, provides a rapid response time, low overall cost, high reliability and ejects the smallest qualitative analysis sample possible to allow adequate analysis and conform to federal regulations involving de minimus release and provide maximum environmental protection. In this case, the valve manifold is electrically or electronically operated, and is preferably formed of stainless steel or other durable material. Since the manual step of coupling and uncoupling the transfer vessel occurs between the transfer vessel fitting and the mating fitting, the valve manifold may also be formed of brass.

It is noted that, since the valve manifold is employed for both sampling and evacuation, all components which are subject to the high vacuum of the evacuation pump must be able to withstand the vacuum levels over repeated cycles. Further, any valves must operate under the varying conditions to which they are normally subject. Preferably, the system is fail-safe, meaning that in most instances, a failure of a portion of the system does not create a condition hazardous to humans or release substantial amounts of refrigerant to the environment. For example, a pressure relief valve may be provided which vents to a refrigerant-impermeable container or vessel, e.g., a bag, rather than to the environment. Another example is that the valving system is configured so that no computer control commands or failure to issue commands, whether intentional or erroneous, may override a separate safety cutoff which prevents dangerous overfilling of storage reservoirs or other vessels. Of course, other fail-safe mechanisms may be provided.

In order to draw a sample, through the valve manifold, mating fitting, fitting, transfer vessel valve and dip tube, to the qualitative analyzer, a sampling pump is provided. The sampling pump draws only a small sample, and preferably includes a purge or deep vacuum function which avoids cross contamination of samples. Thus, the sample pump system may include a vacuum pump function capable of providing a deep 29" vacuum. The sample pump thus provides the pressure differential to transfer the sample material to the sample analyzer. The sample pump may also integrate a calibration function, in which one or more refrigerant gases or contaminants with known characteristics are sampled and qualitatively analyzed. The results of the qualitative analysis are then normalized with the known composition of the calibration source. The analyzer may include linear, linear regression, polynomial, or other standard types of normalization, or may rely on neural networks and/or artificial intelligence-expert systems to determine the quality of the material being sampled. It is noted that the refrigerant being sampled need not be exhaustively analyzed, but rather the general concentration of desired refrigerant determined and the absence of certain types of impurities must be assured.

Generally, the sampling system will analyze the sample after removal of moisture, oil, particulates, and other easily removed substances. The amounts or concentrations of these removed substances may be determined by separate analysis, or estimated. The removal systems generally include filters and reagents, which may become clogged, saturated or spent. A compressed gas cylinder may be provided for purging and null calibration. Alternately, atmospheric air may be used. This cylinder may also become spent. Therefore, the sampling system may include sensors for determining or estimating the exhaustion of the filtering, purifying or calibration elements, and warning or prompting replacement or remediation. Alternately, these components may be provided with an anticipated surplus capacity and replaced on a schedule, such as simultaneous with storage reservoir replacement. Sensors for determining the exhaustion of the removal system may include pressure sensors, optical sensors, and chemical sensors, such as ion-sensitive probes.

After the sample is analyzed, the contents of the transfer vessel are withdrawn. An evacuation pump provides the motive power to withdraw the transfer cylinder contents and transfer the refrigerant to a large, e.g., 1000 pound, storage reservoir cylinder. The evacuation pump is preferably a variable speed electrically driven vane design pump. Where the device is placed outside, or where electrical power is unavailable, a gasoline, Diesel, or natural gas engine may be employed to power the evacuation pump. A pump mounted sensor detects when the transfer cylinder has been emptied of liquid refrigerant and initiates a variable-speed pump speed increase that enables the unit to perform pull down on the remaining refrigerant vapor to a minimum vacuum level of at least 15" Hg and preferably at least 20" Hg, thus completing the regulatory required evacuation of the transfer cylinder.

In order to determine a type and quality of refrigerant in the transfer vessel, a qualitative analyzer is employed. Preferably, this analyzer employs infrared (IR) refrigerant identification technology such a that developed by and available from DuPont/Neutronics, e.g., Refrigerant Identifier II™, Model 9552. The Operation Manual of this device is attached hereto as Appendix A. The qualitative analyzer identifies refrigerant samples taken directly from refrigerant transfer vessels. Refrigerant samples are introduced into the analyzer through a specially designed sample hose. The sample hose minimizes refrigerant sample volume and provides an initial particulate filtration. The sample enters the identifier via a pressure switch controlled solenoid valve. Oil, acids and other contaminates are removed in an internal, heated flash pot. Separated oils and contaminates are automatically flushed from the identifier into an external catch basin which accompanies the analyzer instrument. The catch basin is periodically emptied. The cleansed sample gas is regulated and passed through a coalescing filter which further cleanses the sample of oils and particulates. The clean sample gas travels to the multiple detector Non-Dispersive InfraRed (NDIR) sensing device for analysis. Signals from the sensing device are fed into a microprocessor where the refrigerant type and purity are determined. Depending on the results of this analysis, the system either notifies the user that the transfer cylinder is acceptable for receipt by the machine or rejected. For example, where the system is designed to accept only R22 refrigerant, any other refrigerants, or R22 refrigerant which is contaminated with other refrigerants, are rejected at this stage. The rejection indication may also include further information, such as the reason for rejection. Where a contaminated refrigerant or another refrigerant are presented in a transfer vessel, the transfer vessel may be processed separately in known manner.

The master control for the system interacts with the qualitative analyzer to allow automation of the processes. Thus, the software of the qualitative analyzer need not be modified for integration into the recovery system. Therefore, the various switches and outputs are interfaced with the master control rather than a human user interface. In addition, the master control may be used to maintain the qualitative analyzer in a state of readiness, i.e., warmed up and calibrated. In addition, the master control may provide ventilation to prevent the qualitative analyzer from becoming overheated, or selectively apply power to prolong component life, prevent overheating and reduce power consumption. In addition, the master control allows threshold determination separate from that included within the qualitative analyzer. Thus, the qualitative analyzer processor need be employed to make decisions about whether the system will accept the recovered refrigerant, rather, these decisions may be made in the master control, and updated based on economic and technological considerations which may change over time. In the case of the DuPont/Neutronics Refrigerant Identifier II™, Model 9552, the communication between the master control and the qualitative analyzer may be through the printer port, reconfigured human interface panel, or through another interface, such as a serial port or diagnostics port, which is not normally employed during operation of the device.

In one embodiment, a single large refrigerant storage reservoir vessel is provided, and therefore only a single type of refrigerant is recovered and accepted for recycling or reclamation. In another embodiment, a number of large storage reservoir vessels are provided, and a second valve manifold, associated with the evacuation pump, may be used to selectively route the content of the transfer vessel to one of the storage reservoirs, based on the qualitative analyzer output. For example, different refrigerants may be routed to different storage reservoirs. On the other hand, transfer vessels with different purity levels may be routed to different storage reservoirs to avoid cross contaminating relatively uncontaminated refrigerant with highly contaminated refrigerant, allowing the recycling and reclaiming operations to be made more efficient and optimized. The availability of a number of storage reservoirs may reduce the incidence of rejected transfer vessel contents, requiring separate processing.

In order to determine the quantity of refrigerant in a transfer vessel, a quantitative analyzer in the form of an electronic weight scale is preferably employed. The scale is interfaced to a programmed controller, which generally has a printer output. The three components: qualitative analyzer, quantitative analyzer, and evacuation system, are linked electronically by a control system to perform the overall function of supplying to an accounting system a quantitative input for making a permanent record.

When the machine receives an accept signal from the qualitative analyzer, the controller logs a full transfer vessel weight in memory, possibly along with the qualitative analyzer result. When the machine completes the transfer vessel evacuation stage, another weight will be recorded. A net weight will be calculated. The information may be printed on a ticket along with other information identifying the user. The data may also be recorded on computer disk or stored in memory. Thus, by calculating the tare weight of the transfer vessel and the weight of the contents, the amount of contents may be determined and accounted for. The control system may also operate in a local or wide area computer network environment or through the Internet, allowing centralized control of the recovery operation and accounting. For example, a telecommunications system may be employed to indicate when a storage reservoir is nearing full capacity, to allow efficient scheduling of replacement of the storage reservoir and possible servicing of the system. Further, with centralized accounting, the involvement of the distributor may be reduced, providing a more direct relationship of the originator of the transfer vessel and the recycler, if this is desired.

The refrigerant from the transfer vessel is transferred to a storage reservoir. Preferably, the storage reservoir is a standard 1000 lb. recovery cylinder manufactured to meet requirements of D.O.T. 49 CFR § 178.61 -4BW. In such a cylinder, the maximum liquid refrigerant fill is 80% of volume. The cylinder is equipped with a float activated switch designed to provide a signal to the recovery system to indicate a maximum fill to the 80% threshold. The status of this switch is checked by the programmed controller prior to each use. Calibration of the float may be necessary to prevent accidental overfill from at just less than 80% level. Therefore, the system may include an auxiliary transfer vessel for storage to capture any remaining portion of an evacuation cycle in progress. When the storage reservoir(s) and any auxiliary vessels are not capable of safely accepting further refrigerant, the control will prevent further attempted transfers. On the other hand, the qualitative and quantitative analyzers remain operational, and therefore these components may be employed in the traditional manner of leaving the refrigerant in a transfer vessel to recycling or reclamation in another step, while allowing immediate accounting.

In cases where the system is designed to accept contaminated refrigerant, the accounting system may determine that, instead of having a value, the accepting of the contaminated refrigerant has an associated cost. Since the Federal regulations prohibit discharge of these contaminated refrigerants, the owner must bear the cost of disposal. Thus, the system according to the present invention is not limited to accounting for a positive value of refrigerant, and it should be understood that, where the terms accounting or value are used herein, these may be positive or negative values to be accounted.

In general, the storage reservoir is a standard 1000 lb. U.S. D.O.T. approved shipping vessel, as discussed above, which does not itself include a quantitative contents gage or level. Thus, where this information is desired, a weight sensor or another type of device may be employed. Generally, however, a stop fill switch will be used to prevent overfill, and any other level is inconsequential. It is often considered cost prohibitive to mount a level transmitter on the reservoir tank. Overfilling the reservoir, or any refrigerant tank, is a serious safety violation that could result in death or injury therefore an alternate means to keep track of the reservoir level is desirable. Therefore, according to the present invention, the programmed controller may be used to keep track of the amount of refrigerant which has been transferred to the storage reservoir in an ongoing manner. This may be used as a backup calculation to the float switch, and the programmed control locks out the recovery pump in the event of a total weight exceeding the maximum allowed. It is noted that the typical float valves employed are subject to errors due to oil accumulation, and therefore a backup system is desirable. A reset switch in a secure area of the machine or a special code entered by keyboard or other data entry system may be used to zero the total with each new replacement storage reservoir.

In order to sense the contents of the storage reservoir, and in addition to the float switch and/or calculation of storage reservoir contents, a weight sensor may be provided to detect the weight of the storage reservoir vessel. Further, since the liquid line on the storage reservoir shell will have an abrupt change in heat capacity and acoustic properties, these characteristics may also be used to sense the amount of contents. Finally, as the storage reservoir nears full capacity, the pressure-volume characteristics of the flow into the storage reservoir may be detectably altered, allowing a sensor in the refrigerant conduit, on the evacuation pump, or in another portion of the system to detect the volume of refrigerant in the storage reservoir.

One particular aspect of the invention is that, by calculating an amount of refrigerant in a transfer vessel and by qualitative analysis, a valuation may be performed on the refrigerant content of the transfer vessel, which may allow accounting between the distributor and the recycler. In general, the apparatus according to the present invention will operate in controlled environment and facilities of a HVACR wholesale supplier, to alleviate the burden of small recovery cylinder management. The value determination of the recovered refrigerant will thus depend on the identification/quality of the commodity, the current market value of the commodity, the amount of the commodity and possibly the contractor's relationship with the wholesale supplier.

The programmed control of the present system is capable of the performing a complete and detailed valuation of the refrigerant content of the transfer vessel and keeping an account of that value. However, in some cases, this functionality is not needed. In fact, the weight of any transfer vessel contents evacuated may be sufficient information to be used by the wholesale supplier to assign the value and maintain the accounting. An alternate arrangement allows the wholesale supplier to input data on his rates for recovered refrigerant from his customers or from individual or classes of customers, such that the control system may complete the assignment of value to the transferred refrigerant, so that the printed receipt would include a monetary value assignment.

After the transfer vessel is emptied, the user generally receives a verification of the transaction, e.g., a receipt printed by a printer. The machine may also store the information electronically for downloading to the wholesale supplier's data processing system, and for other purposes, such as tracking refrigerant sources and impurities. In this case, each user may be identified by an individualized code which could be keyed in, read through a bar code reader, magnetic stripe reader, smart card reader, spoken into a microphone, or other known identification input methods.

A permanent, hard copy of all transactions during a timeperiod may be transmitted by the programmed controller by communications through, for example, a serial port or other communication system, such as a modem or the Internet. Typically, the data is downloaded to an external computer with a printer, or alternately the on-board tape receipt printer may, upon prompt, provide the full list of transactions to the wholesale supplier at storage reservoir exchange. Thus, the system need not be integrated into a large electronic system and thus may stand alone, producing human comprehensible output of important information.

The apparatus is provided within a frame, which supports the various elements and shields the inner workings from the external environment. The frame preferably includes a housing, for both cosmetic reasons and for protection of the device from external influences and users from the inner workings of the device. The housing is preferably a gusset supported metal skin, which may be functional. Generally, the apparatus will be located in an industrial or office environment, but may be adapted for placement outside. One access door is provided for access to the storage reservoir by a forklift for exchange thereof. Another, smaller access door or portal is provided for placement, by the user, of the 30–50 pound transfer vessel on the electronic scale. In general, the system provides two alternatives. First, the apparatus may accept a righted cylinder, requiring the use of the dip-tube equipped liquid port, as discussed above. Alternatively, the apparatus may accept the transfer vessel in an inverted position, with a hose attachment to the so-called vapor port. In either case, the door is preferably closed and internally latched prior to operation of the machine. The overall appearance of the device will therefore be similar in size to that of a refrigerated beverage vending machine, with a user interface system, e.g., data input keyboard and/or card swipe located towards the upper right portion, similar to where coins are normally entered in a coin venting machine. The ticket or receipt printer, mounted internally, ejects the ticket in an area where a dollar bill feed is located on a vending machine. A miniature CRT, or flat panel display, may also be mounted near the input device. A top mounted "full" light and warning annunciator (with squelch or acknowledgment of alarm) or chime may also be provided to assist the operator or wholesale supplier in monitoring the status of the machine.

A third door may be provided on the apparatus for routine maintenance activities, including removal of a filled waste oil container from the qualitative analyzer, printer paper refill or filter change.

The device according to the present invention may also integrate a recycling system, similar to that disclosed in Zugibe, U.S. Pat. No. 5,377,499, expressly incorporated herein by reference. This integral recycling system allows a more accurate determination of the refrigerant quantity by allowing a measurement of the recoverable refrigerant amount, while ensuring that the storage reservoir is filled only with purified refrigerant. Impurities, depending on their type, may be stored separately, vented, or cause the system to reject the refrigerant. The system according to U.S. Pat. No. 5,377,499 includes a heat exchanger having heated purified refrigerant has for heating unpurified refrigerant liquid.

These and other objects will become apparent. For a full understanding of the present invention, reference should now be made to the following detailed description of the preferred embodiments of the invention as illustrated in the accompanying drawings.

BRIEF DESCRIPTION OF THE DRAWINGS

The invention will now be described with reference to the accompanying drawings, in which.

DETAILED DESCRIPTION OF THE PREFERRED EMBODIMENTS

Figure 1:
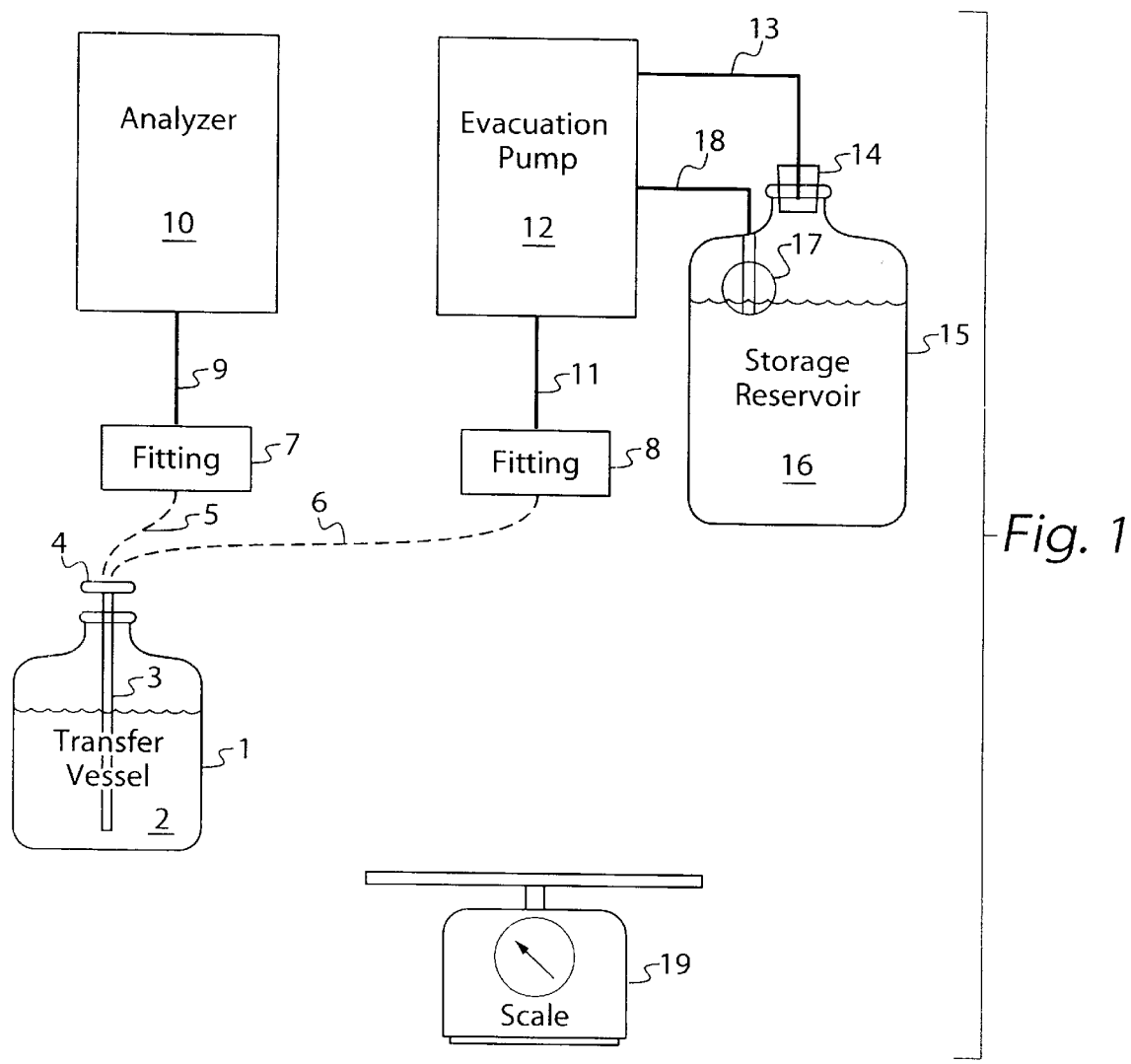
FIG. 1 is a block diagram of a prior art refrigerant recovery system.
Figure 2:
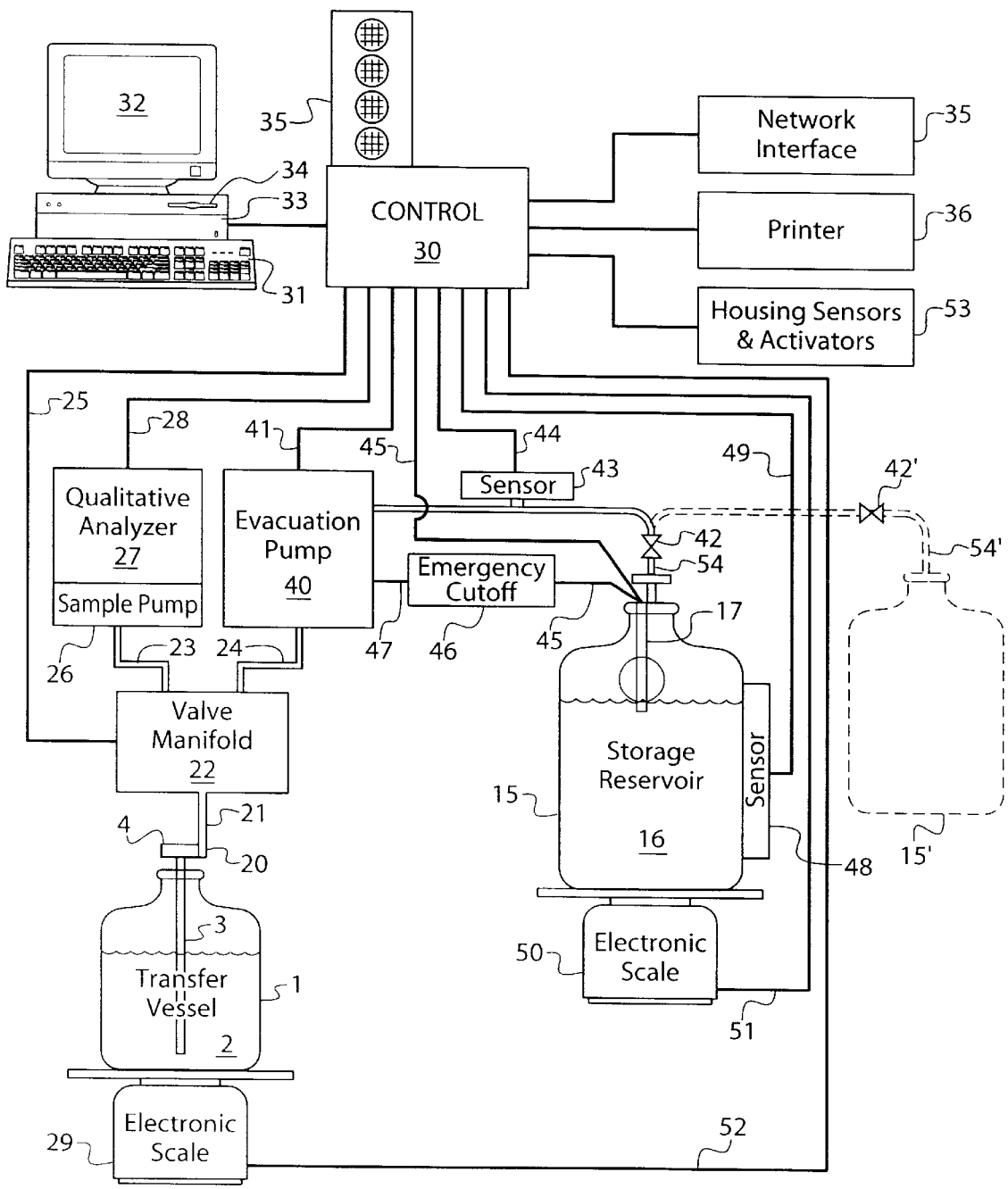
FIG. 2 is a block diagram of the refrigerant recovery system according to the present invention.

The detailed preferred embodiments of the invention will now be described with respect to the drawings. Like features of the drawings are indicated with the same reference numerals.

The transfer vessel 1 may be a typical U.S. Department of Transportation ("U.S. D.O.T.") approved metal container having a capacity of 30–50 lb. refrigerant. The transfer vessel 1 includes a combined liquid/vapor valve 4 located on top and optionally a reed switch used to prevent overfilling. The transfer vessel 1 valve 4 fitting mates with a SAE standard J639 fitting, which is $7/16$ inch, 20 thread, which is used for all common refrigerants except R-134a. An internal dip tube 3 allows direct removal of liquid 2 without inverting the transfer vessel 1. As noted above, the transfer vessel 1 may include other features, not shown.

A dip tube 3, a plastic or metal hollow elongated cylindrical structure located internal to the transfer vessel 1, is provided. An external valve 4 assembly is mounted on top of the transfer vessel 1, from which the dip tube 3 extends downward. The dip tube 3 terminates close to the bottom of the transfer vessel 1, to allow fluid 2 removal without vaporization. Operation of the combined liquid/vapor valve 4 allows liquefied refrigerant to be sucked or drawn out of the transfer vessel without manually inverting the cylinder. For this purpose, a vacuum sufficient to lift the liquid refrigerant 2 out of the transfer vessel 1 is sufficient. However, after the liquid refrigerant 2 is below the bottom of dip tube 3, the transfer vessel 1 must be inverted, or a vacuum drawn within the transfer vessel 1 to vaporize the refrigerant. Alternately, the transfer vessel 1 may be mounted inverted and all contents removed through the so-called vapor passage, which is in communication with the top of the transfer vessel 1. Further, as will be noted below, the tank must be completely purged of residual refrigerant down to a vacuum of at least 15 inches of mercury after removal of the liquid refrigerant 2.

A valve manifold 22 is provided which connects to the transfer vessel. Optimally, where the contents of the transfer cylinder are known, the valve may be connected to a desired fitting. Thus, for example, R-134a transfer vessels would interface to the recovery system through a separate fitting, of a different type. The mating fitting of the valve manifold 22 is formed of stainless steel.

The valve manifold 22 allows a single connection between the transfer vessel 1 valve 4 and the recovery system for initially sampling the refrigerant quality and subsequently allowing complete refrigerant 2 withdrawal. The components of the valve manifold 22 are preferably electrically operated solenoid valves, but pneumatic or hydraulically operated valves may also be used. The valve housing is preferably formed of stainless steel or brass, with minimum void volumes.

A sampling pump 26 is provided which draws a small volume of the liquid refrigerant 2 to the qualitative analyzer 27. This sample is drawn from the transfer vessel, through the dip tube 3, valve 4, fitting 20, conduit 21, valve manifold 22, and conduit 23, to the sampling pump 26, which is physically integrated with the qualitative analyzer 27. The sampling pump 26 is associated with filters and dryers for removing particulates and moisture from the sample. The sample is heated in an internal flash pot to volatilize the refrigerant and separate the refrigerant from any oil and/or acids. The oil and/or acids are automatically purged from the system through a separate exit port, not shown, into a catch basin. This purge port is also used to blow any gas through the sampling system to avoid cross contamination of samples and allow calibration of zero refrigerant concentration. In the present case, it is preferable that the system purge the entire valve manifold between uses. The cleansed sample gas is regulated and passed through a coalescing filter which further cleanses the sample of oils and particulates. The clean sample gas travels to the multiple detector Non-Dispersive InfraRed (NDIR) sensing device for analysis. The preferred qualitative analyzer 27 is a DuPont/Neutronics, Refrigerant Identifier II™, Model 9552. The sample enters the identifier via a pressure switch controlled solenoid valve.

Output signals from the sensing device of the qualitative analyzer 27 are fed into a microprocessor where the refrigerant type and purity are determined. Depending on the results of this analysis, the system normally either notifies the user that the transfer cylinder is acceptable for receipt by the machine or rejected. The rejection may also include further information, such as the reason for rejection. Preferably, the master control 30 receives or intercepts this information and processes it to apply its own standards. Thus, the predetermined acceptance criteria of the preferred qualitative analyzer, e.g., 98% purity, do not limit the criteria applied by the recovery system as a whole, which may have lower or higher acceptance criteria, or criteria which vary for different refrigerants or impurities or be alterable as conditions change.

Since the recovery system may be used intermittently, a calibration system is preferably provided to supply a gas stream as an internal reference having a known composition to the analyzer system to ensure accuracy of readings. Preferably, this calibration system is tightly coupled to the qualitative analyzer, and does not pass through the main valve manifold. This increases the efficiency of the calibration system and improves speed of operation. The calibration system is controlled by the master control 30. The calibration gas is selectively shunted to the analyzer input, and the analyzer output adjusted to correctly read the refrigerant type and concentration. The calibration may be a two point calibration (zero and span) or more complex, such as various refrigerants and/or known contaminated gases. The calibration cycle is preferably automatically triggered based on time since last calibration, environmental factors or changes, usage, and/or other factors.

A single large refrigerant storage reservoir 15 is provided, and therefore only a single type of refrigerant 2 is accepted for recovery. However, it can easily be envisioned that a plurality of storage reservoirs 15, 15' are provided, which may be used for increased capacity of a single refrigerant or the ability to recover different refrigerants. In this case, valves 42, 42' are provided which direct the refrigerant to the appropriate storage reservoir 15, 15', based on the qualitative analyzer output of refrigerant type, purity, and/or sensed or calculated remaining capacity of a storage reservoir. The evacuation pup is controlled by the master control 30 through a connection 41. This control may be at a high level, i.e., commence operation and cease operation, or at a low level, i.e., with motor driver circuitry integral to the master control 30.

After the sample is analyzed by the qualitative analyzer 27, and the refrigerant liquid 2 meet predetermined criteria, e.g., greater than 98% purity of volatile gas refrigerant, refrigerant of the correct type, and the absence of impurities which would be difficult to separate, the contents of the transfer vessel 1 are withdrawn. In this case, the valve manifold 22 remains connected to the transfer vessel 1 through the conduit 21, fitting 20 and valve 4. An evacuation pump 40 provides the motive power to transfer the refrigerant 2 from the transfer cylinder 1 to a large, e.g., 1000 pounds, storage reservoir 15. The evacuation pump 40 is preferably a variable speed electric driven vane design pump. A pump mounted sensor detects when the transfer cylinder 1 has been emptied of liquid refrigerant 2 and initiates a pump speed increase that enables the unit to perform pull down on the remaining refrigerant vapor to a minimum vacuum level of at least 15 inches or mercury, thus completing the regulatory required evacuation of the transfer cylinder.

In order to determine the quantity of refrigerant in a transfer vessel 1, a quantitative analyzer in the form of an electronic weight scale 29 is preferably employed. This scale is, for example, a strain gage weight measurement system. The scale is interfaced to the master control 30, and through the master control 30 to a printer 36. Of course, the scale may be directly interfaced to a printer. The scale 29 is used to allow an accounting of the amount of refrigerant 2 recovered from the transfer vessel 1 by recording the weight before and after refrigerant 2 removal. The printer 36 is one means for making a permanent record of the transaction.

When the master control 30 indicates that the refrigerant 2 is of sufficient quality and of the correct type, by way of an output 28 from the qualitative analyzer 27, the master control 30 logs a full transfer vessel 1 cylinder weight in memory, possibly along with the qualitative analyzer 27 result. When the system completes the transfer vessel 1 evacuation stage, another weight is recorded. A net weight is then calculated as the difference between the full and empty weights of the transfer vessel 1. The information is printed on a ticket by the printer 36 optionally along with other information identifying the user, which is input upon commencing the process through a terminal device 33 having a keyboard 31, display 32 and magnetic storage device 34 (floppy disk). The data also will be recorded on a computer disk 34. Thus, by calculating the tare weight of the transfer vessel 1 and the weight of the contents, the amount of contents may be determined and accounted for.

The refrigerant from the transfer vessel 1 is transferred to a storage reservoir 15, which is a standard 49 C.F.R. § 178.61 -4BW compliant 1000 lb. recovery cylinder. In such a cylinder, the maximum liquid refrigerant fill is 80% of volume. The cylinder is equipped with a float activated switch 17 designed to provide a signal to the recovery system to indicate a maximum fill to the 80% threshold. The status of this switch 17 is checked by the master control 30 prior to each use. Calibration of the float switch 17 may be necessary to prevent accidental overfill from at just less than 80% level. Therefore, the system may include an auxiliary transfer vessel (not shown) for storage to capture any remaining portion of an evacuation cycle in progress, to allow completion thereof. When the storage reservoir(s) and any auxiliary vessels are not capable of safely accepting further refrigerant, the master control 30 will prevent further attempted transfers. On the other hand, the qualitative analyzer 27 and quantitative analyzer 29 remain operational, and therefore these components may be employed in the traditional manner of leaving the refrigerant in a transfer vessel 1 for recycling or reclamation in separate step, while allowing immediate accounting (with estimation of the transfer vessel 1 contents.)

A pressure sensor 43 may be provided on the conduit 54 between the evacuation pump 40 and the storage reservoir 15, connected to the master control 30 through line 44. This pressure sensor allows determination of whether the evacuation pump is pumping fluid, and possibly whether the storage reservoir is near full by spectral and echo analysis of the pressure signal.

In order to provide additional indication of the storage reservoir 15 content 16 amount, various gauges may optionally be employed. For example, the weight of the storage reservoir 15 may be determined by a scale 50, with an output 51 to the master control 30, to determine the amount of refrigerant 16 in the storage reservoir 15. Another example is a heat sensitive linear sensor 48, such as a series of thermistors, semiconductor sensors, or thermocouples, which measure a difference in temperature which occurs along the liquid gas line when the refrigerant is condensing or vaporizing, and communicate with the master control 30 through a sensor cable 49. A liquid crystal sensor may be used to provide a visual indication of the fluid line under certain circumstances. Because overfilling of the storage reservoir 15 is hazardous, a fail safe emergency cutoff 46 is preferably provided, bypassing the master control 30 with a direct connection 45 between the float switch 17 and the evacuation pump 40. A known level transmitter (not shown) may also be mounted on the storage reservoir 15 tank.

In addition to tracking storage reservoir 15 fullness with sensors, the master control may also keep track of the amount of refrigerant 16 which has been transferred to the storage reservoir 15 in an ongoing manner. Thus, one or more backup systems may be employed to prevent overfilling, by which the master control 30 locks out the recovery evacuation pump 40 in the event of a total weight exceeding the maximum allowed. A reset switch in a secure area of the machine or a special code entered by keyboard or other data entry system may be used to zero the total with each new replacement storage reservoir 15.

The tracking of storage reservoir 15 content 16 by the master control allows a second level of accounting, between the recycling company and the distributor. The recovery system generally is situated at the facilities of a distributor, who generally accounts directly with his customers for recovered refrigerant. The recovery system according to the present invention therefore alleviates the burden of small recovery cylinder management on the distributor, while maintaining the service. The value determination of the recovered refrigerant will thus depend on the identification/quality of the commodity, the current market value of the commodity, the amount of the commodity and possibly the contractor's relationship with the wholesale supplier.

The master control 30 of the present system is capable of performing a complete and detailed valuation of the refrigerant 2 content of the transfer vessel 1 and keeping an account of that value. However, in some cases, this functionality is not needed. In fact, the weight and acceptance/rejection status of the transfer vessel 1 refrigerant 2 contents may be sufficient information to be used by the wholesale supplier to assign the value and maintain the accounting. An alternate arrangement allows the wholesale supplier to input data on his customers' rates such that the receipt would include a direct monetary value assignment.

After the transfer vessel 1 is emptied, the user receives a verification of the transaction, e.g., a receipt printed by the printer 36. The master control 30 may also store the information electronically for downloading to the wholesale supplier's data processing system, and for other purposes, such as tracking refrigerant sources and impurities. In this case, each users may be identified by an individualized code which could be keyed in through the keyboard 31, read through a bar code reader, magnetic stripe reader, smart card reader, spoken into a microphone, or other known identification input methods.

A permanent, hard copy of all transactions during a timeperiod may be transmitted by the master control 30 by communications through, for example, a serial port or other communication system, such as a network interface 37, modem or the Internet. Typically, the data is transferred or downloaded to an external computer, or alternately the on-board tape receipt printer 36 may, upon prompt, provide the full list of transactions to the wholesale supplier at storage reservoir 15 exchange.

Figure 3:
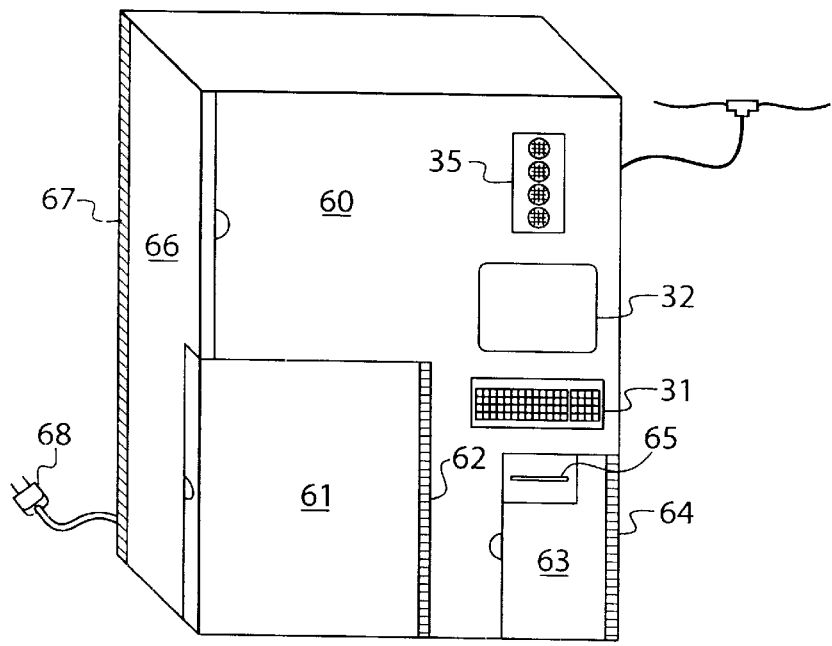
FIG. 3 is a perspective view of a system according to the invention, showing the user interface and access systems.

The apparatus is provided within a frame, which supports the various elements and shields the inner workings from the external environment. Generally, the apparatus will be located in an industrial or office environment, but may be adapted for placement outside. The workings of the apparatus are thus encased within a gusset supported metal skin 60. One access door 66, with a rear hinge 67 is provided for access to the storage reservoir 15 by a forklift for exchange thereof. Another, smaller access door 61 or portal is provided for placement, by the user, of the 30–50 pound transfer vessel 1 on the electronic scale 29. In general, the system provides two alternatives. First, the apparatus may accept a righted cylinder, requiring the use of the dip-tube equipped liquid port, as discussed above. Alternatively, the apparatus may accept the transfer vessel in an inverted position, with a hose attachment to the vapor port. In either case, the smaller access door 61 is preferably closed and internally latched prior to operation of the machine. For this purpose, the master control 30 is connected to housing sensors and actuators 53 to ensure housing 60 integrity and safety. The overall appearance of the device will therefore be similar in size to that of a refrigerated beverage vending machine, with a user interface system, e.g., data input keyboard 31 and/or card swipe located towards the upper right portion, similar to where coins are normally entered in a coin venting machine. The ticket or receipt printer 36, mounted internally, ejects the ticket in an area 65 where a dollar bill feed is located on a vending machine. A CRT 32, or flat panel display, may also be mounted near the input device. A top mounted "full" light and warning enunciator 35 (with squelch or acknowledgment) or chime may also be provided to assist the operator or wholesale supplier in monitoring the status of the machine. The system is powered, for example, by a 120VAC or 220VAC circuit through a connection 68, indicated schematically in FIG. 3 as a line cord.

A third door 63 is provided on the apparatus for routine maintenance activities, including removal of a filled waste oil container from the qualitative analyzer, printer paper refill or filter change.

VALVE MANIFOLD

Figure 4:
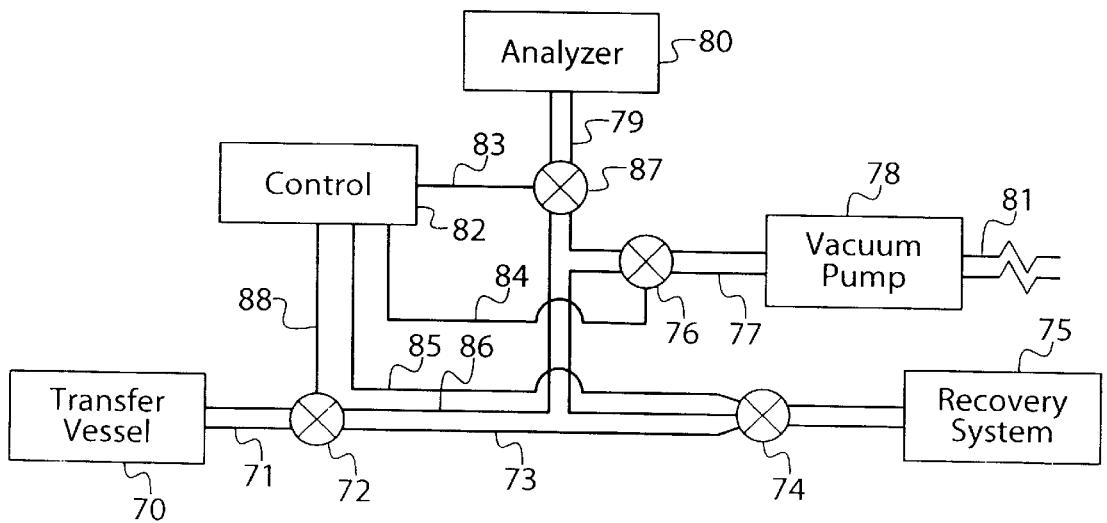
FIG. 4 is a schematic diagram of the valve manifold system according to the present invention.

The valve manifold is shown in more detail in FIG. 4. The control 82 controls each of the valves 72, 74, 76, 87 through control lines 88, 85, 84, 83 respectively. Each of the valves 72, 74, 76, 87 is an electrical solenoid valve.

The transfer vessel 70 is connected through a fitting and hose 71 to a valve 72. This valve 72 selectively allows flow from the transfer vessel 70 to the valve manifold 73. A valve 87 is provided between the valve manifold 73 and the qualitative analyzer 80 through sample hose 79. When the valve 87 is open, a further set of valves and pumps within the qualitative analyzer 80 are operative to sample the refrigerant in the transfer vessel 70. After sampling is complete, the valve 87 is closed. Prior to sampling, the vacuum pump 78 may be activated and valve 76 opened to purge the valve manifold 73 through conduit 77 to reduce contamination. A purge gas, such a air or nitrogen, may be supplied from the qualitative analyzer 80 through the valve 87 to assist in purging.

When the transfer vessel is being evacuated, valves 72 and 74 are open, allowing refrigerant to flow through the valve manifold 73 to the recovery systems 75, which includes an evacuation pump. While variable speed evacuation pumps are available to draw a vacuum down to 15 inches or mercury, a secondary vacuum pump 78 may be provided which draws a deeper vacuum. The output of the vacuum pump 78 may be condensed and fed to the recovery system, or if sufficiently low amounts of refrigerant, purged to the atmosphere.

INTEGRAL RECLAMATION APPARATUS

Figure 6:
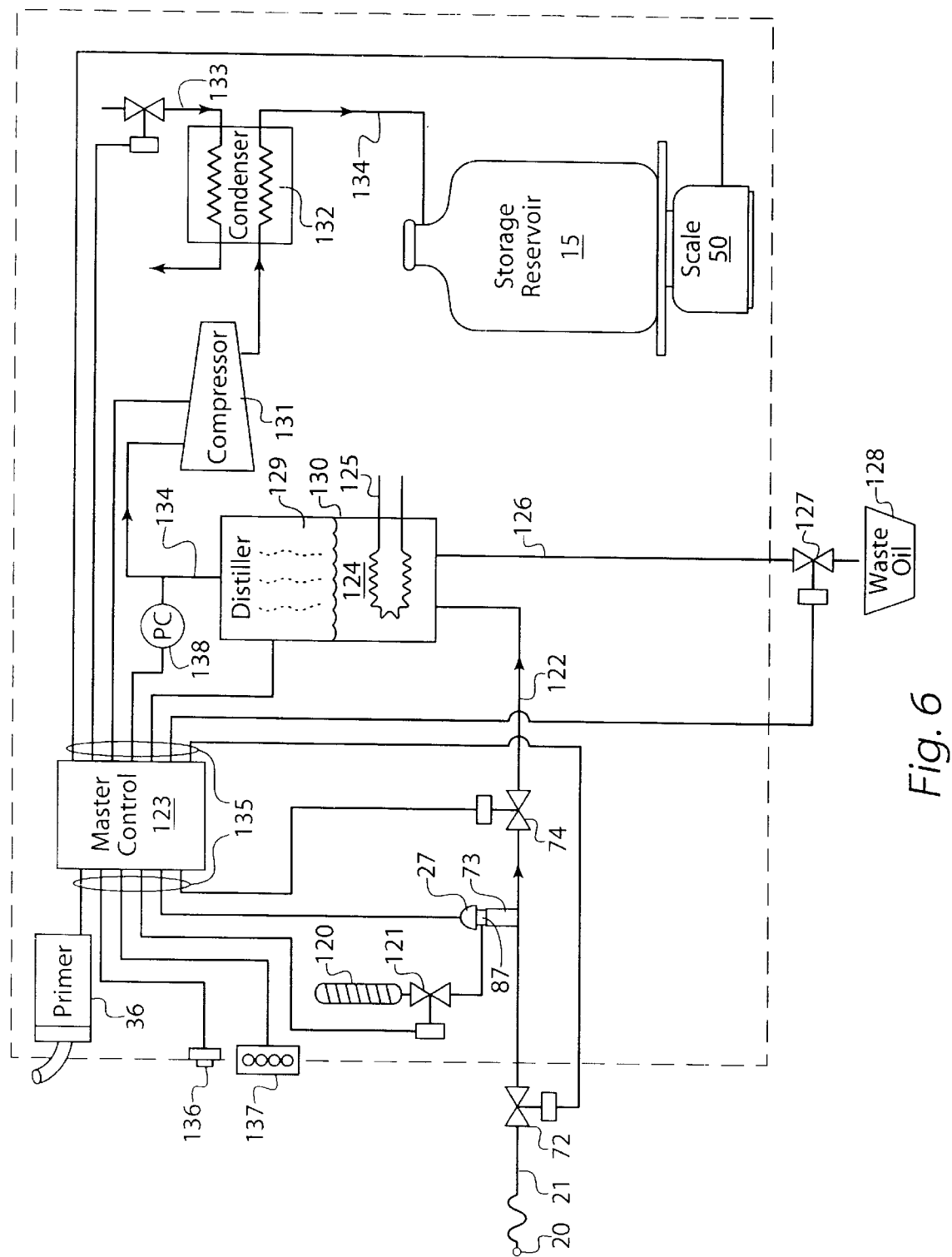
FIG. 6 is a block diagram of a refrigerant recovery system according to the present invention which includes an integral reclamation device.

As shown in FIG. 6, an integral distillation apparatus may be provided to reclaim refrigerant within the recovery device. Thus, a device of this type may also be used for dispensing reclaimed refrigerant as well, so long as the purity of reclaimed refrigerant is sufficient. As shown, the fitting 20 feeds the contents of the refrigerant transfer vessel through the conduit 21 to the valve 72, which selectively allows refrigerant into the manifold 73. The qualitative analyzer 27 is also connected to the valve manifold 73 through valve 87. A calibration gas source 120 is selectively connected to the valve manifold 73 by valve 121. The operation is initiated by depression of a start button 136. If the qualitative analyzer 27 indicates the correct type of refrigerant and sufficient purity, the valve 74 is opened which allows refrigerant to be drawn from the transfer vessel 1, through the fitting 20, conduit 21, valve 72, manifold 73, and valve 74 to conduit 122, under control of the master control 123. The refrigerant 124 is drawn into a distillation apparatus 130. A heater 125 heats the refrigerant to distill off refrigerant while leaving non-volatile oils and acids, which are ultimately purged through line 126 and valve 127 into a waste vessel 128. The volatilized refrigerant 129 is drawn by a compressor 131 to a cold plate 132 which cools and condenses the refrigerant with cold water 133. The condensed refrigerant passes through line 134 into storage reservoir 15. In this case, the master control 123 controls each of the valves, pumps and devices, through a wiring harness 135. The weight of recovered refrigerant, in this case, is determined by an electronic scale 50 based on an increase of weight of the storage reservoir 15. The weight difference in the storage reservoir is then output to a printer 36. Status indicators 137 may be illuminated to provide indication of status and reclamation progress. For a typical 30 pound transfer vessel, the reclamation process may be completed within 5 minutes. The pressure in line 139 between the distiller 130 and the compressor 131 is measured by pressure transducers 138, which is used to control the progress of the distillation and recovery process.

METHOD OF OPERATION

The system operates according to a control program, with minimal user intervention. The following is a sequence of operation for an embodiment of the invention.

Upon initialization, which may occur for every user, every day, periodically, or according to another scheme, the system performs a status check, self diagnostic check, and calibration 101. If these tests product appropriate results, the system is then available for use. Of particular note is that the system checks to see if the storage reservoir is filled to capacity, e.g., about 80% full. This over-capacity check is also continuously performed, even when the machine is at rest. In the event of a failure 103, the system is unavailable, with the exception that a full storage reservoir condition will still allow analysis of transfer vessel contents.

Figure 5:
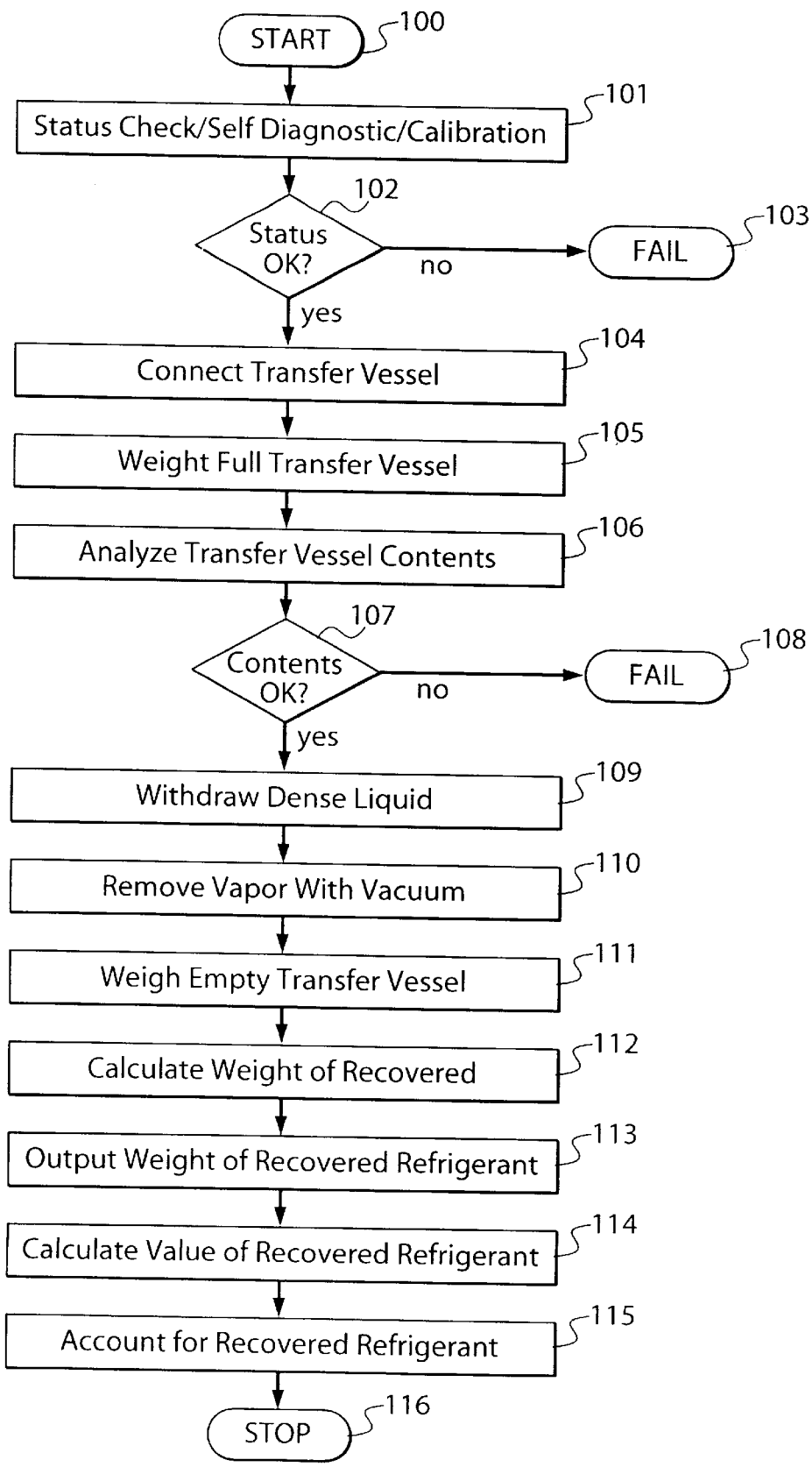
FIG. 5 is a flow diagram of a refrigerant recovery method according to the present invention.

In use, the initial steps of operation (not shown in FIG. 5 may optionally include identification of the user, the type of refrigerant expected, accounting information, and warm-up and calibration of the system as necessary. In this case, the user should be authorized, the refrigerant of the correct type, and the account identification appropriate. However, as these steps are optional, as such information may be verified automatically and/or handled manually after recovery.

The user inserts the transfer vessel within the machine, on an electronic scale mechanism. The valve manifold system is connected to the transfer cylinder 104. The system may be set up in one of two ways. First, the transfer vessel may be placed upright, with the valve manifold system connected to the dip tube. However, in some instances, the dip tube is defective, blocked with contaminants, or bent. Further, the bottom of the dip tube may not withdraw all of the liquid refrigerant, prolonging the evacuation operation. Therefore, as an alternative, the transfer vessel may be inverted, with the valve manifold connected to the vapor port of the transfer vessel. In this way, gravity feeds all of the liquid refrigerant to the valve manifold and bypasses the dip tube. It is noted that in the inverted configuration, dense contaminants are withdrawn first, and may leave a residue in the valve manifold.

After the transfer vessel is connected to the valve manifold and placed on the scale and weighed 105, the user presses a start button. A sample is drawn from the valve manifold with a sampling pump to a DuPont Neutronics qualitative analyzer 106. The transfer vessel door is latched closed, and a first timer started. A visual indication of the status and sequence of the machine may be provided to the user, such as a "sampling" lamp.

The preferred Neutronics qualitative analyzer 27 has its own control, with a user interface. The inputs and outputs are redirected through the master control 30. Thus, the Neutronics device asks for "connect hose", causing the main control to close valves 76, 74 and open valves 72 and 87. Generally, the result of the qualitative analysis will be a "pass" from the Neutronics device; however, in the event of a "fail" 108, such as due to wrong refrigerant or cross contamination, the system closes valve s 87 and 72, the first timer stopped, the door unlatched, and the user is prompted to remove the transfer vessel with the unacceptable contents intact. A light is illuminated which indicates "contaminated cylinder".

In the likely event of a "pass", the first timer is stopped, a second timer started, a start weight recorded from the scale (see 105), valves 72 and 74 opened, a recovery relay (which activates the evacuation pump 40) activated, and a light illuminated which indicates "Refrigerant OK—recovery in process".

The recovery process using the standard evacuation mode 109 continues until the pressure in the vessel is about 15 inches of mercury, at which point a vacuum pump 78, capable of drawing a vacuum of about 29 inches of mercury is connected 110 through valve 76 to the manifold, with valve 74 closed. When the cylinder is drawn to a pressure of less than about 20 to 29 inches of mercury, the second timer is stopped, the recovery relay deactivated, and valves 72, and 76 closed. The weight of the cylinder after recovery is measured 111, and the difference between the stored starting weight and the final weight, e.g., the tare weight of the empty cylinder, determined 112, indicating the weight of refrigerant removed. The door is unlatched, and a light illuminated indicating "cylinder empty". A receipt is printed indicating the amount of refrigerant withdrawn 113, and possibly other identifying information.

The timers are part of a fail-safe mechanism which halts an operation if any portion appears to be taking too long, suggesting machine malfunction. The maximum times for the various operations are determined, and with a margin of safety programmed as alarm triggers.

The determined weight difference is then optionally further corrected for the presence of water and oil, by the output of the qualitative analyzer which determines a purity level of the refrigerant. This corrected weight is then used to determine the value of the refrigerant withdrawn 114 and thus account for that value 115. The printed receipt may thus include an analysis of the refrigerant and the corrected weight of pure refrigerant.

There has thus been shown and described novel refrigerant recovery and recycling systems and methods which fulfill all the objects and advantages sought therefor. Many changes, modifications, variations, combinations, subcombinations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A recovery device for recovering a composition from a supply vessel to at least one storage container, comprising:
    (a) a conduit communicating with the supply vessel;
    (b) an analyzer for assessing a quality of a composition contained in the supply vessel through the conduit;
    (b) a sensing system for determining a quantity of the composition for recovery;
    (c) means for withdrawing the composition from the supply vessel through the conduit;
    (d) a storage device for storing withdrawn composition; and
    (e) a processor for receiving the assessment from said analyzer and said quantity from said sensing system and automatically generating a weighted value of the composition of the supply vessel based thereon.

2. The recovery device according to claim 1, wherein said processor automatically controls a sequence of said sensing system and said withdrawing means.

3. The recovery device according to claim 1, wherein said sensing system determines a quantity of composition before withdrawal from the supply vessel.

4. The recovery device according to claim 1, wherein said weighted value generated by said processor comprises an economic value of composition in the supply vessel.

5. The recovery device according to claim 1, wherein the composition comprises a volatile composition.

6. The recovery device according to claim 1, wherein the composition comprises a volatile refrigerant.

7. The recovery device according to claim 1, wherein the recovery device prevents environmental release of composition and said withdrawal means draws a vacuum in the supply vessel.

8. The recovery device according to claim 1, wherein said storage device pools composition recovered from a plurality of supply vessels.

9. The recovery device according to claim 1, further comprising a fractional distillation system for purifying composition prior to storage in the storage device.

10. The recovery device according to claim 1, wherein the composition in the supply vessel is at least partially liquid, further comprising a purification system for purifying the composition to separate a first liquid component from a second miscible component.

11. The recovery device according to claim 1, further comprising a gauge for determining a quantity of composition in the storage device.

12. The recovery device according to claim 1, wherein said processor controls said recovery device to prevent mixing of composition of different types to a single storage device.

13. The recovery device according to claim 1, wherein said processor analyzes said assessed quality of the composition and selectively controls withdrawal based on said assessed quality.

14. The recovery device according to claim 1, further comprising a plurality of storage devices, the composition being withdrawn from the supply vessel into a respective one of the plurality of storage devices based on said assessed quality.

15. The recovery device according to claim 1, wherein said analyzer determines a proportion of a constituent in the composition, and said processor references a composition constituent value table, to determine a weighted value for the constituent composition based on a proportion of the constituent and a sensed quantity of composition.

16. The recovery device according to claim 1, further comprising an automated valve manifold for selectively controlling a composition flow from the supply vessel to said analyzer and the storage device, respectively.

17. An automated composition recovery method, for recovering a composition from a supply vessel to at least one storage container, comprising the steps of:
   (a) providing a fluid interface to the supply vessel
   (b) assessing a quality of a composition contained in the supply vessel through the fluid interface;
   (c) determining a quantity of the composition for recovery;
   (d) withdrawing the composition from the supply vessel through the fluid interface;
   (e) storing withdrawn composition in a storage vessel; and
   (f) receiving the assessment and the quantity and automatically generating a weighted value of the composition based thereon.

18. The method according to claim 17, wherein the weighted value comprises an economic value of composition in the supply vessel.

19. The method according to claim 17, further comprising the step of controlling the withdrawal based on the determined quality.

20. The method according to claim 17, wherein the composition comprises a volatile composition and a miscible liquid phase.

* * * * *